United States Patent
Basu

(10) Patent No.: US 10,010,296 B2
(45) Date of Patent: Jul. 3, 2018

(54) SYSTEMS AND METHODS FOR X-RAY CT SCANNER WITH RECONFIGURABLE FIELD OF VIEW

(71) Applicant: MORPHO DETECTION, LLC., Newark, CA (US)

(72) Inventor: Samit Kumar Basu, Fremont, CA (US)

(73) Assignee: Morpho Detection, LLC, Newark, CA (US)

( * ) Notice: Subject to any disclaimer, the term of this patent is extended or adjusted under 35 U.S.C. 154(b) by 628 days.

(21) Appl. No.: 14/585,822

(22) Filed: Dec. 30, 2014

(65) Prior Publication Data

US 2016/0187503 A1    Jun. 30, 2016

(51) Int. Cl.
*A61B 6/04* (2006.01)
*A61B 6/03* (2006.01)
(Continued)

(52) U.S. Cl.
CPC .......... *A61B 6/0428* (2013.01); *A61B 6/4429* (2013.01); *A61B 6/588* (2013.01);
(Continued)

(58) Field of Classification Search
CPC .. A61B 6/00; A61B 6/03; A61B 6/032; A61B 6/035; A61B 6/04; A61B 6/0407; A61B 6/0428; A61B 6/42; A61B 6/4266; A61B 6/44; A61B 6/4411; A61B 6/4429; A61B 6/58; A61B 6/588; A61B 2560/00; A61B 2560/04; A61B 2560/0443; G01T 1/00; G01T 1/16; G01T 1/24; G01T 1/243; G01T 1/29; G01T 1/2907; G01T 1/2914; G01T 1/2928; G01T 1/2964; G01T 1/2971; G01T 1/2985; H05G 1/00; H05G 1/02; H05G 1/08; H05G 1/26; H01L 25/00;
(Continued)

(56) References Cited

U.S. PATENT DOCUMENTS 4,649,277 A    3/1987 Terra et al.
5,457,724 A *  10/1995 Toth .................. A61B 6/032
                                              378/205

(Continued)

FOREIGN PATENT DOCUMENTS

EP    0846961 A1    6/1998
WO    2004019279 A2    3/2004
WO    2005004722 A2    1/2005

OTHER PUBLICATIONS

International Search Report for GB1522511.3, dated Mar. 31, 2016.

*Primary Examiner* — Anastasia Midkiff
(74) *Attorney, Agent, or Firm* — Armstrong Teasdale LLP

(57) ABSTRACT

A gantry assembly for use with an imaging system is provided. The gantry assembly includes an x-ray source and a modular detector assembly that includes a plurality of selectively removable detector modules. A first detector module of the plurality of detector modules is mounted at a first distance from the x-ray source and a second detector module of the plurality of detector modules is mounted at a second distance from the x-ray source. The first distance is different from the second distance. The gantry assembly is configured to image objects using both a first field of view and a second field of view that is larger than the first field of view.

14 Claims, 15 Drawing Sheets

(51) Int. Cl.
*G01T 1/24* (2006.01)
*A61B 6/00* (2006.01)
*G01T 1/29* (2006.01)

(52) U.S. Cl.
CPC .............. *G01T 1/243* (2013.01); *A61B 6/035* (2013.01); *A61B 6/0407* (2013.01); *A61B 2560/0443* (2013.01); *G01T 1/2985* (2013.01)

(58) Field of Classification Search
CPC ..... H01L 25/10; H01L 25/105; H01L 25/115; H01L 25/16; H01L 25/18; H01L 27/144; H01L 27/1446; H01L 27/146; H01L 27/14601; H01L 27/14618; H01L 27/14658; H01L 27/14676; H01L 27/148; H01L 27/14806; G21K 1/00; G21K 1/02; G21K 1/04
See application file for complete search history.

(56) References Cited

U.S. PATENT DOCUMENTS

| | | | |
|---|---|---|---|
| 5,717,212 A | 2/1998 | Fulton et al. | |
| 6,700,948 B2* | 3/2004 | Hoffman | A61B 6/032 250/370.09 |
| 6,768,782 B1* | 7/2004 | Hsieh | A61B 6/032 378/4 |
| 6,873,678 B2* | 3/2005 | Hoffman | A61B 6/4233 250/370.09 |
| 7,054,409 B2* | 5/2006 | Ross | A61B 6/032 250/370.09 |
| 7,062,006 B1 | 6/2006 | Pelc et al. | |
| 7,233,644 B1* | 6/2007 | Bendahan | G01N 23/046 378/57 |
| 7,433,443 B1* | 10/2008 | Tkaczyk | A61B 6/032 378/19 |
| 7,848,480 B2* | 12/2010 | Nakanishi | A61B 6/032 378/4 |
| 7,945,012 B2 | 5/2011 | Ye et al. | |
| 8,433,119 B2 | 4/2013 | Deykoon | |
| 8,731,634 B2* | 5/2014 | Birman | A61B 6/0471 378/195 |
| 2004/0097800 A1 | 5/2004 | Crosetto | |
| 2006/0210015 A1 | 9/2006 | Pelc et al. | |
| 2013/0039458 A1* | 2/2013 | Ikhlef | G01T 1/2985 378/19 |
| 2014/0010343 A1 | 1/2014 | Basu et al. | |

* cited by examiner

SYSTEMS AND METHODS FOR X-RAY CT SCANNER WITH RECONFIGURABLE FIELD OF VIEW

BACKGROUND

The embodiments described herein relate generally to imaging systems, and more particularly, to imaging systems with a reconfigurable field of view.

At least some known computer tomographic (CT) imaging systems have a predetermined field of view (FOV) that is generally chosen to be as small as possible while still meeting requirements for the particular imaging application. Because the FOV has a direct influence on the size of a detector array required, as well as the design and construction of the remainder of a gantry, selecting the FOV is important for the overall dimensions of the imaging system. Accordingly, the FOV drives the cost of the imaging system, as the number of detectors required to achieve a given FOV generally increases in proportion to a diameter of the FOV. Hence, all things being equal, a system with a larger FOV will be more expensive than an equivalent system with a smaller FOV.

In cases of explosives detection or non-destructive testing, the problem is further complicated by the integration of the imaging system into the infrastructure of a manufacturing or transportation site. For example, the installation of an explosives detection system into an airport may be conducted with a certain FOV in mind. However, changes in the operation of the airport may result in a need to increase the FOV at a later time. Existing solutions require a wholesale replacement of the initial system with a larger system containing a larger FOV. Accordingly, at least some known imaging systems are designed with a fixed FOV because the cost of changing the FOV is substantial. As FOV requirements change, however, at least some known imaging systems are unable to be easily reconfigured to have a larger FOV.

BRIEF SUMMARY

In one aspect, a gantry assembly for use with an imaging system is provided. The gantry assembly includes an x-ray source and a modular detector assembly that includes a plurality of selectively removable detector modules. A first detector module of the plurality of detector modules is mounted at a first distance from the x-ray source and a second detector module of the plurality of detector modules is mounted at a second distance from the x-ray source. The first distance is different from the second distance. The gantry assembly is configured to image objects using both a first field of view and a second field of view that is larger than the first field of view.

In another aspect, an imaging system is provided. The imaging system includes a gantry assembly that includes an x-ray source and a modular detector assembly. The modular detector assembly includes a plurality of selectively removable detector modules. A first detector module of the plurality of detector modules is mounted at a first distance from the x-ray source and a second detector module of the plurality of detector modules is mounted at a second distance from the x-ray source. The first distance is different from the second distance. A conveyor extends through a tunnel defined through the gantry assembly. The imaging system is configured to image objects using both a first field of view and a second field of view that is larger than the first field of view.

In yet another aspect, a method for imaging an object is provided. The method is performed using a gantry assembly that includes an x-ray source and a modular detector. The modular detector has a plurality of selectively removable detector modules. A first detector module of the plurality of detector modules is mounted at a first distance from the x-ray source and a second detector module of the plurality of detector modules is mounted at a second distance from the x-ray source. The first distance is different from the second distance. The method includes altering a number of detector modules in the modular detector such that a field of view of the gantry assembly changes from a first size to a second size, and imaging the object using the field of view having the second size.

DETAILED DESCRIPTION

The embodiments described herein provide a CT imaging system that is capable of being reconfigured to operate using different fields of view. By incorporating a modular detector array having a compact geometry, the field of view is quickly reconfigurable. This allows the field of view to be adjusted at a factory or in the field, reducing costs as compared to at least some known imaging systems. Further, an insert may be utilized to facilitate positioning an object within the current field of view.

Figure 1:
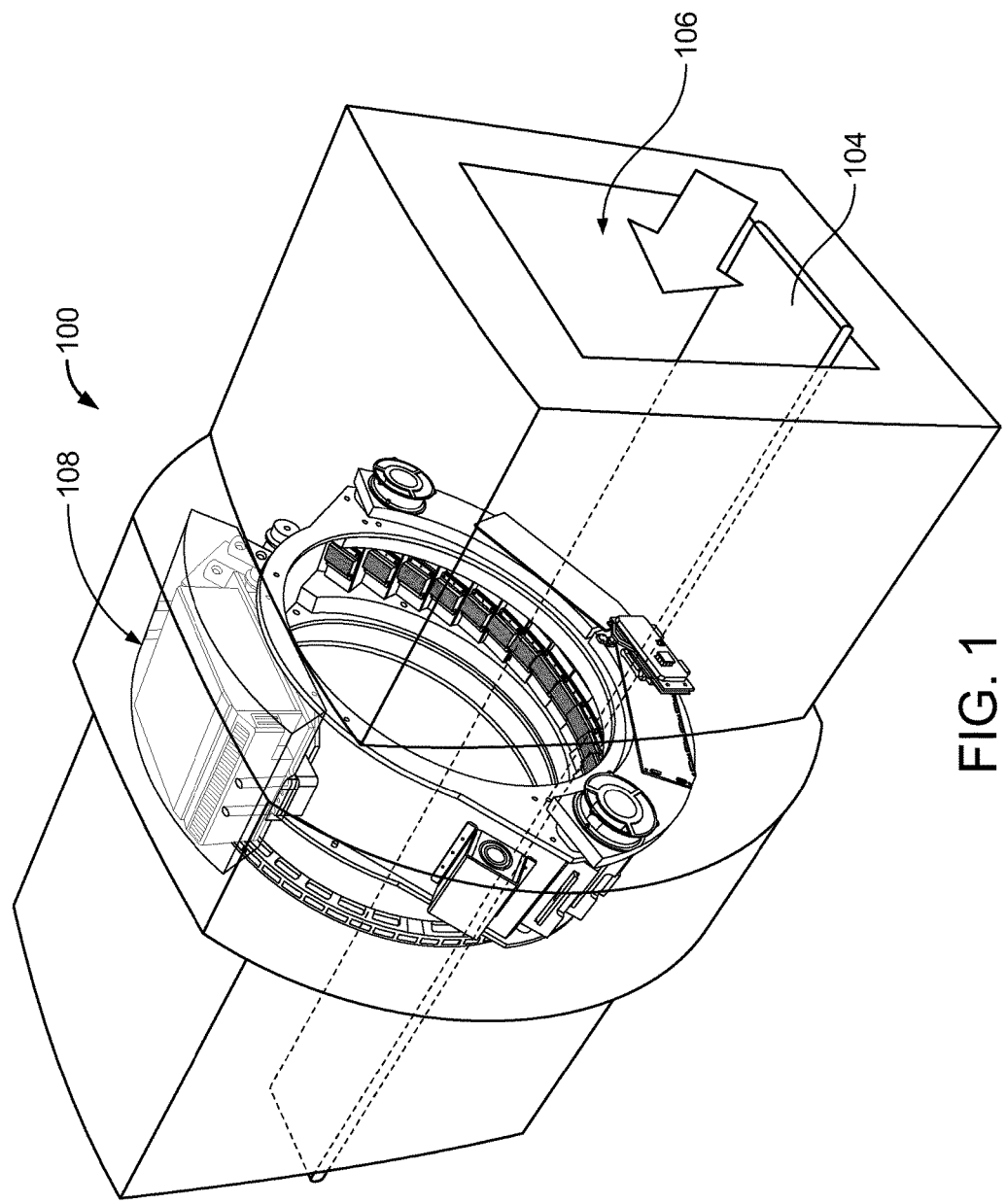
FIG. 1 is a perspective view of an exemplary imaging system.

FIG. 1 is a perspective view of an exemplary imaging system 100. The imaging system 100 is an x-ray CT imaging system and may be, for example, a baggage scanning system for viewing items in baggage passing through imaging system 100. For example, imaging system 100 may be used to detect contraband (e.g., explosives, drugs, weapons, etc.) located in the baggage. Imaging system 100 includes a tunnel 106 and a conveyor 104 extending through tunnel 106.

Figure 2:
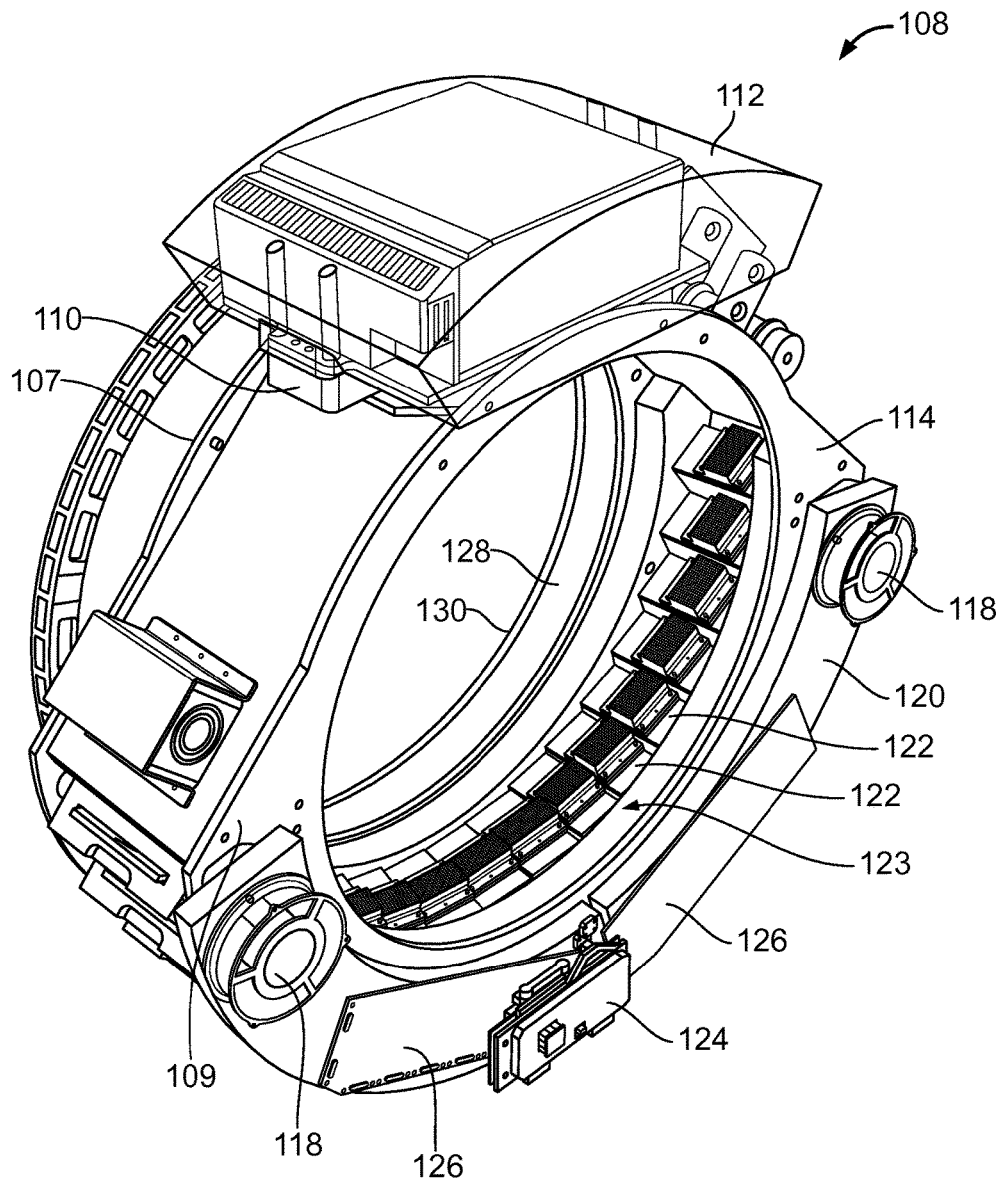
FIG. 2 is a perspective view of an exemplary gantry assembly that may be used with the imaging system shown in FIG. 1.

FIG. 2 is a perspective view of an exemplary gantry assembly 108 that may be used with imaging system 100 (shown in FIG. 1). A radiation source 112, which emits x-rays, is mounted to a gantry frame 114 by an x-ray mount 110. In the exemplary embodiment, gantry frame 114 is a steel bolted structure with a bore of approximately 85 centimeters in diameter. The interior surface of gantry frame 114 is lined with lead. In this embodiment, x-ray mount 110 is cast steel with a lead cast window. X-ray mount 110 is configured to allow for position adjustment along an axis that is parallel to a length of tunnel 106 (the Z-axis).

On a first side 107 of gantry assembly 108, as shown in FIG. 2, are a bearing 128 and a slip ring 130. Bearing 128 allows gantry assembly 108 to rotate around an object to be imaged. In the exemplary embodiment, gantry assembly 108 is capable of rotating continuously, at approximately 150 rotations per minute. Slip ring 130 allows data signals and power to be transmitted between gantry assembly 108 and a remainder of imaging system 100, as will be appreciated by those skilled in the art. Attached to a second side 109 of gantry frame 114, opposite first side 107, is a plenum 120, which operates as a heat sink. Mounted to plenum 120 are global back planes 126, which contain electronics and circuitry for proper operation of gantry assembly 108, power management converter 124, for powering the components of gantry assembly 108, and fans 118 to transfer heat away from gantry assembly 108.

A plurality of detector modules 122 are arranged in an array 123, inside gantry frame 114. Detector modules 122 receive x-ray beams emitted from radiation source 112 and convert the x-ray beams to electrical signals representing image data. Detector modules 122 are positioned in the gantry assembly 108 with an axis of symmetry running from radiation source 112 to the center of central detector module 122. In alternative embodiments, there is an even number of detector modules, and an axis of symmetry runs from the radiation source to a point between two central detector modules. As explained below, detector modules 122 are arranged to increase an inner diameter of gantry assembly 108 relative to an outer diameter of gantry assembly 108, when compared to prior CT imaging systems. The benefit is that imaging system 100 is given a smaller footprint while maintaining or increasing the size of objects, such as baggage, that can be scanned. Accordingly, imaging system 100 may be referred to as having a "compact geometry." Further detector modules 122 are selectively removeable to adjust a field of view (FOV) of imaging system 100, as described herein.

Figure 3:
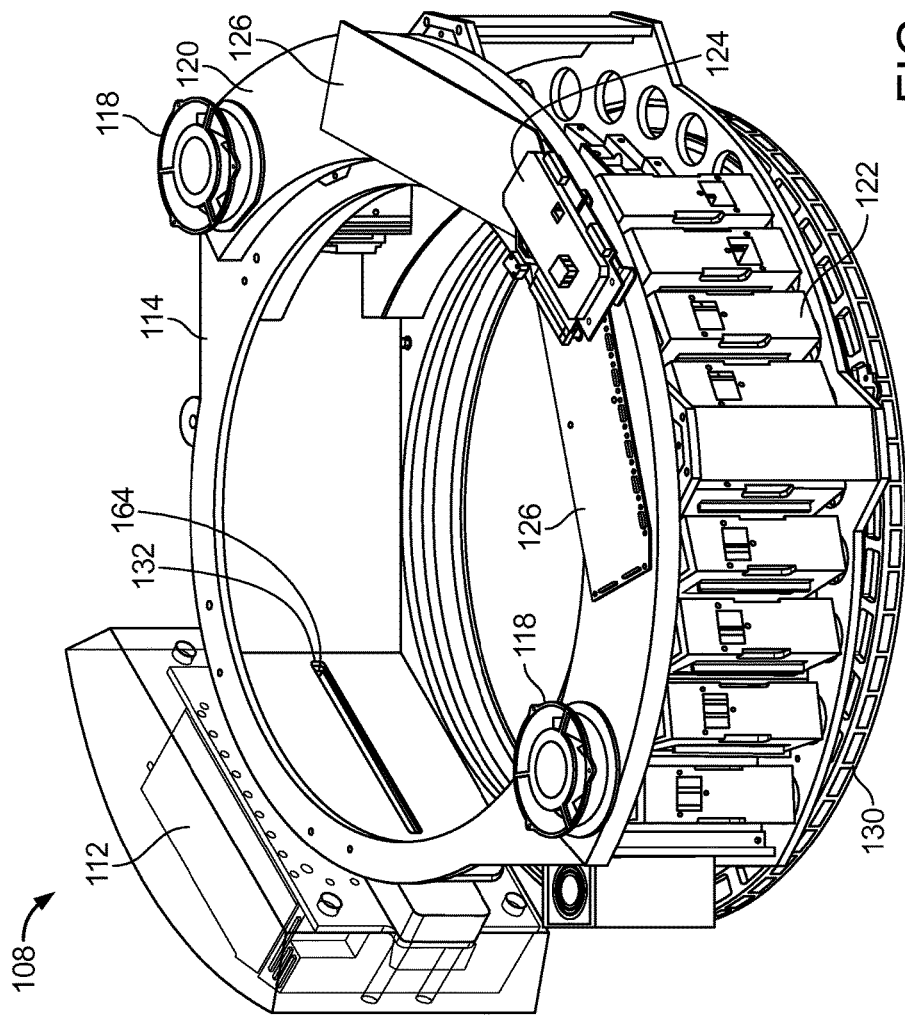
FIG. 3 is a perspective view of the gantry assembly shown in FIG. 2.
Figure 4:
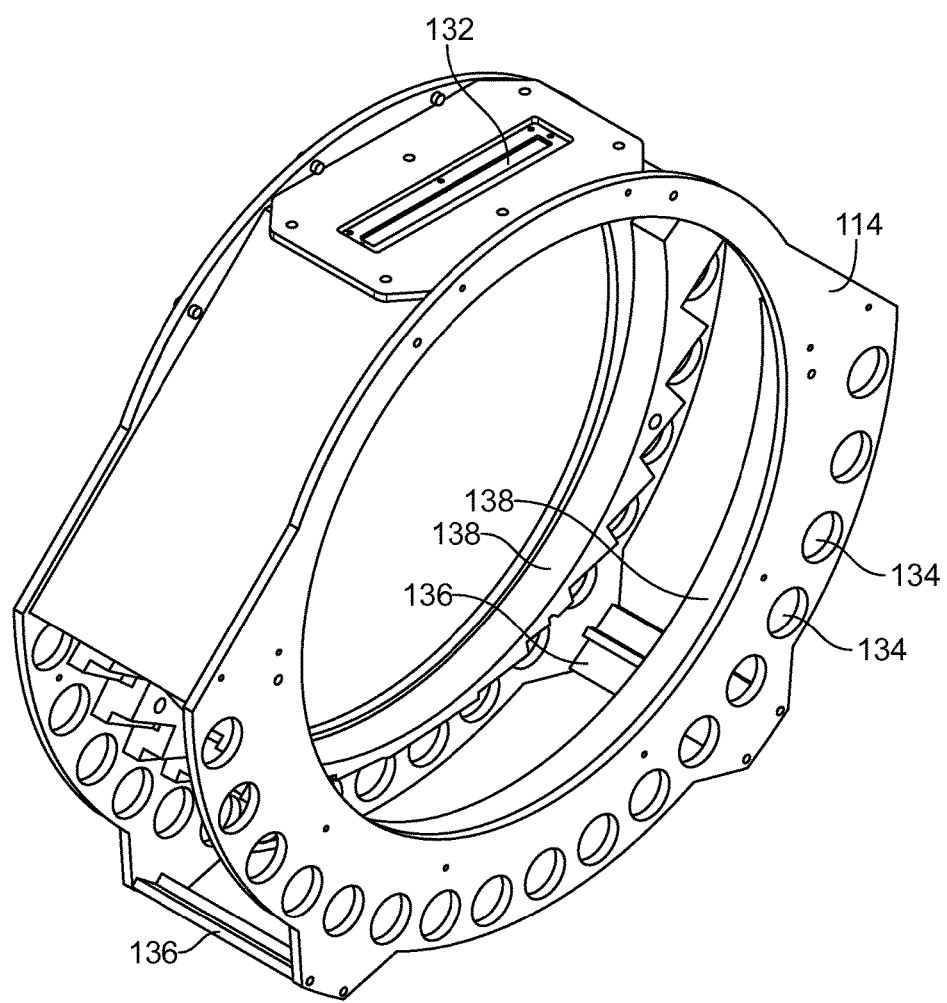
FIG. 4 is a perspective view of an exemplary gantry frame that may be used with the gantry assembly shown in FIG. 2.

FIG. 3 is another perspective view of gantry assembly 108. An opening 132 in gantry frame 114 allows x-ray beams from radiation source 112 to be emitted into gantry assembly 108. The x-rays are emitted in a cone beam that intersects the entire tunnel 106. An x-ray seal with a pre-collimator 164 of x-ray attenuating material is located between radiation source 112 and opening 132. As shown in FIG. 3, slip ring 130 is attached to one side of gantry assembly 108 opposite plenum 120 and two global back planes 126 are mounted to plenum 120. Power management converter 124 is connected to global back planes 126. Fans 118 mounted to plenum 118 help transfer heat away from plenum 120 and gantry assembly 108 in general. Detector modules 122 are positioned such that during cone-to-parallel rebinning, resolution loss is minimized. As shown in FIG. 3, some detector modules 122 are removed to expose a portion of underlying gantry frame 114. In FIG. 4, discussed below, the gantry frame 114 is shown without any other components attached.

FIG. 4 is a perspective view of gantry frame 114. Opening 132 allows x-rays from radiation source 112 to be emitted into gantry assembly 108 in a cone beam. Included on opposite interior sides of gantry frame 114 are positioning rails 138 that provide a mounting point for each detector module 122 in gantry assembly 108. Included along opposite outer sides of gantry frame 114 are cooling holes 134 that facilitate heat transfer away from gantry frame 114. Also included in gantry frame 114 are torsion force stiffeners 136, which provide structural support for gantry frame 114.

Figure 5:
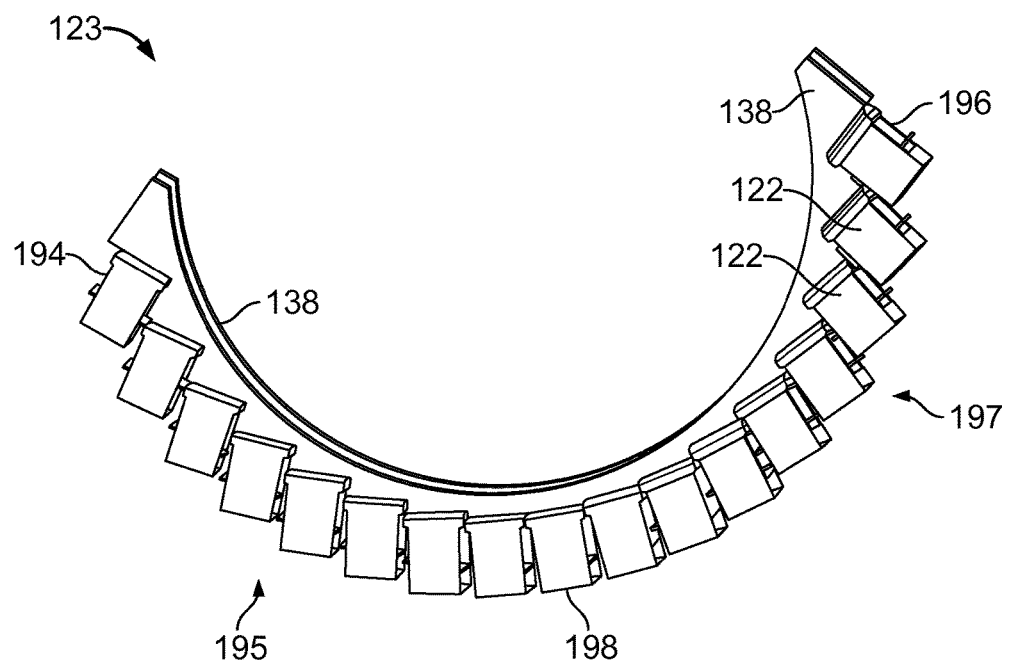
FIG. 5 is a perspective view showing an exemplary array of detector modules that may be used with the gantry assembly shown in FIG. 2.

FIG. 5 is a perspective view showing array 123 of detector modules 122. Detector modules 122 are positioned along positioning rails 138. In this exemplary embodiment, 17 detector modules are included in array 123. Array 123 includes a first end 194 and an opposite, second end 196. Additionally, array 123 is divided into a first half 195, extending from a center 198 of array 123 to first end 194, and a second half 197, extending from center 198 of array 123 to second end 196. Other embodiments may include fewer or more detector modules and the total number of detector modules may be odd or even. In the exemplary embodiment, one detector module 122 is located at center 198 such that it is directly opposite radiation source 112. Mirrored pairs of identical detector modules 122 extend outwards on either side. Detector modules 122 are gapped to allow for manufacturing tolerances in gantry assembly 108.

Figure 6:
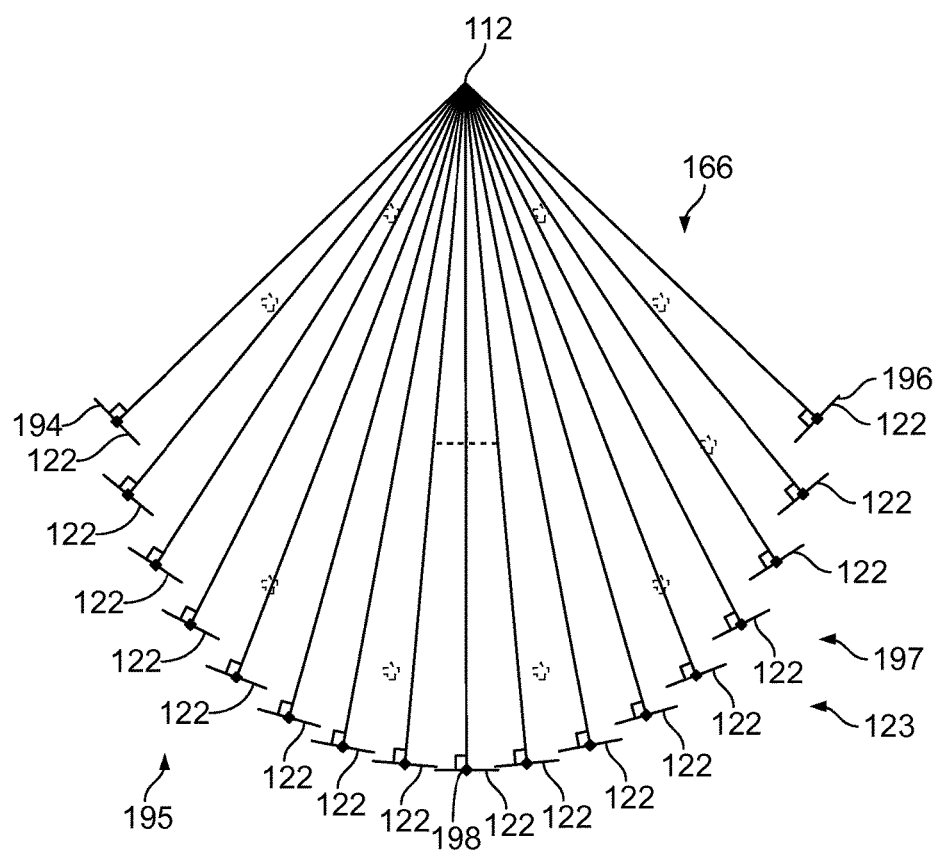
FIG. 6 is a diagram showing the paths of x-rays emitted by a radiation source to the detector modules shown in FIG. 5.

FIG. 6 is a diagram showing x-ray beams 166 emitted by radiation source 112 towards detector modules 122. As can be seen, each detector module 122 is positioned so that the center of its collimator is normal to incident radiation bisecting detector module 122. Adjacent edges of adjacent detector modules 122 are angularly spaced from each other. The angular spacing of the centerlines of beams 166 bisecting adjacent detector modules 122 decreases moving from ends 194 and 196 of array 123 of detector modules 122 to the center 198.

Starting from detector module 122 at center 198, shown in FIG. 6, and moving outwards, each detector module 122 is a different distance from radiation source 112. That is, detector module 122 at center 198 is the furthest away from radiation source 112 and detector modules 122 along the first half 195 are closer to radiation source 112. Moving from center 198 towards first end 194, each successive detector module 122 is closer to radiation source 112 than the previous detector module 122. Each detector module 122 along first half 195 has a corresponding detector module 122 on second half 197, located at the same distance from radiation source 112. That is, each detector module 122, except detector module 122 located at center 198, is part of a mirrored pair. The result of this arrangement is a smaller outer diameter of gantry assembly 108 as compared to CT imaging systems which have a constant radiation source to detector distance (SDD). As a result of this arrangement of separate detector modules 122, the inner diameter of gantry assembly 108 is maximized relative to the outer diameter of gantry assembly 108.

The compact geometry described with regards to FIGS. 1-6 may be implemented in an x-ray CT imaging system with a reconfigurable field of view (FOV), as described herein. FIGS. 7-15 are schematic diagrams comparing different FOVs in a gantry using a non-compact geometry and a gantry including a compact geometry in accordance with the systems and methods described herein.

Figure 7:
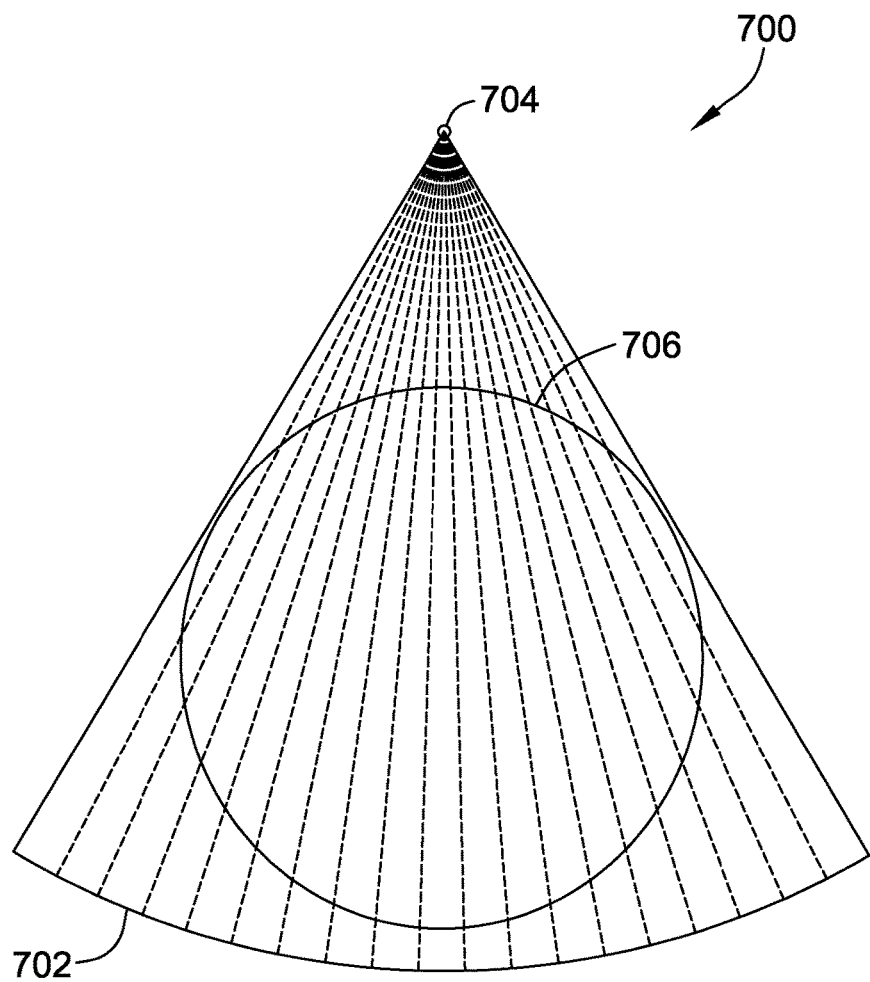
FIGS. 7-14 are schematic diagrams comparing different fields of view in a gantry using a non-compact geometry and a gantry including a compact geometry.

FIG. 7 is a schematic diagram of a gantry 700 that includes detector modules 702 placed at a constant distance from an x-ray source 704. The design of gantry 700 is based on two parameters: the distance between x-ray source 704 and an isocenter of gantry 700, and the distance between x-ray source 704 and detector modules 702. Given these two parameters and a desired first FOV 706, the geometry of gantry 700 is essentially fixed.

When attempting to reconfigure gantry 700 to make first FOV 706 larger or smaller, the x-ray source 704 to isocenter distance should remain fixed, as changing this distance is relatively impractical. Even if x-ray source 704 can be moved relative to the isocenter, the shape of the rest of gantry 700 (i.e., the position of detector modules 702) will be unchanged, resulting in inadequate illumination of detector modules 702.

Figure 8:
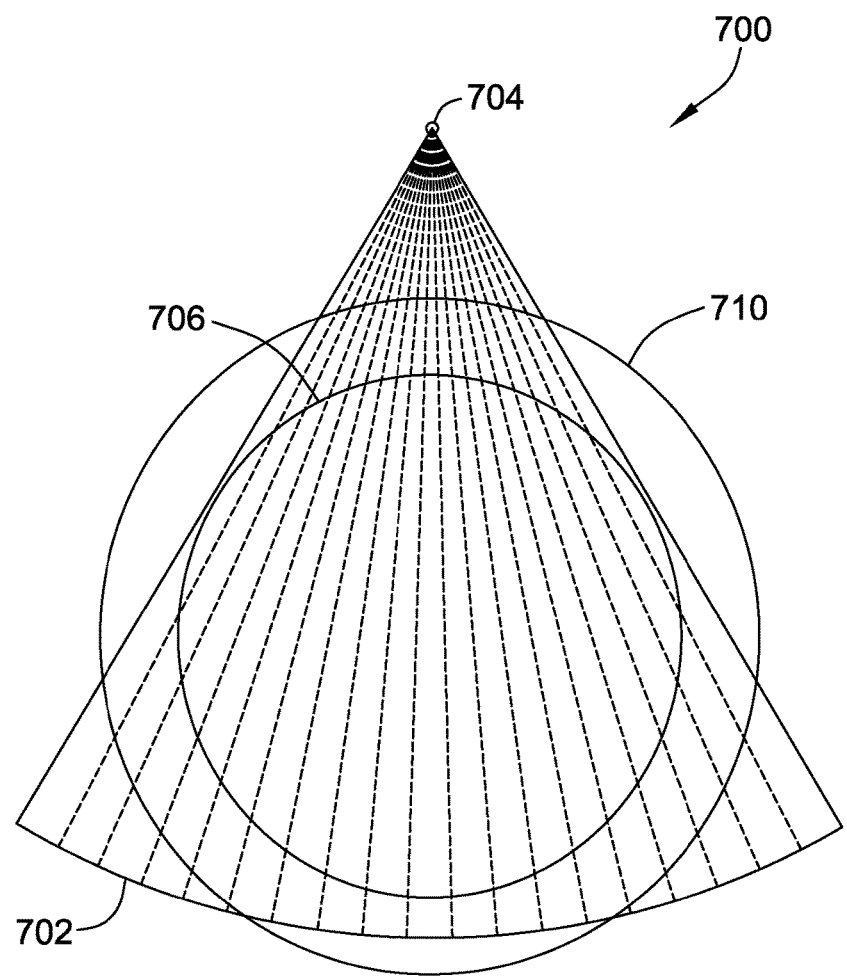

Referring now to FIG. 8, consider trying to modify gantry 700 accommodate a second FOV 710 that it 30% larger than first FOV 706 with the same gantry design. As shown in FIG. 8, to accommodate second FOV 710, detector modules 702 need to be moved further from x-ray source 704, as the detector arc intersects second FOV 710.

Figure 9:
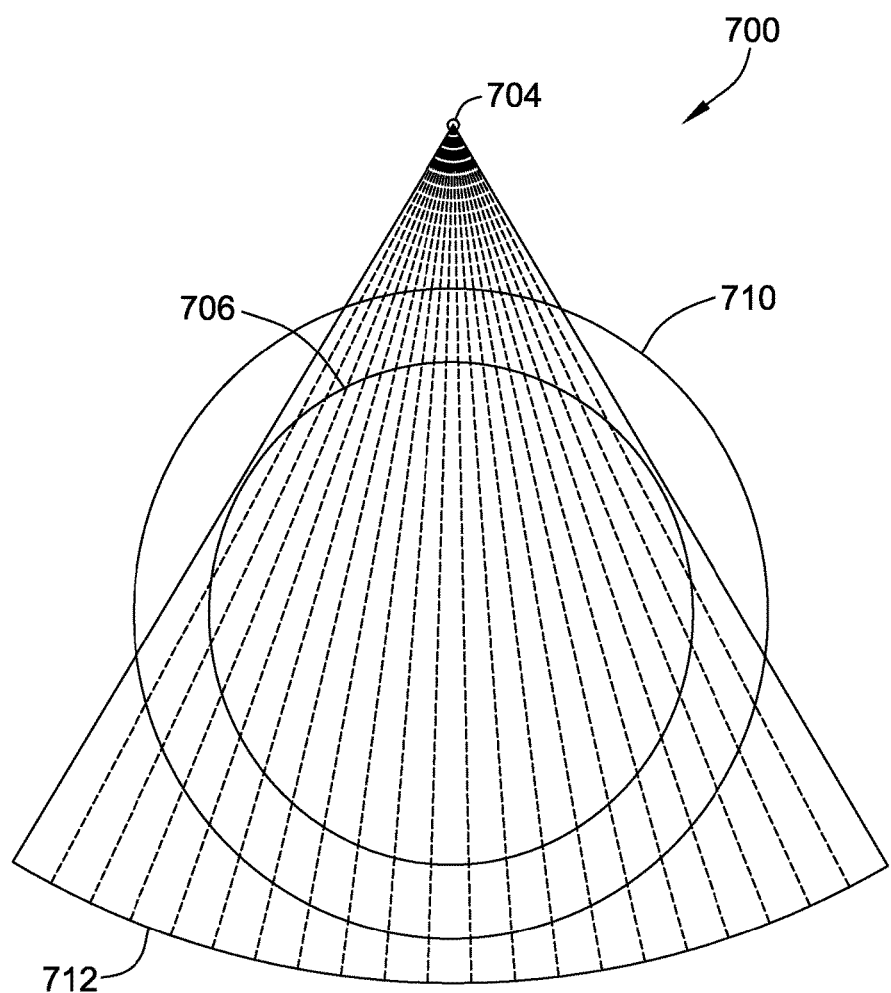
Figure 10:
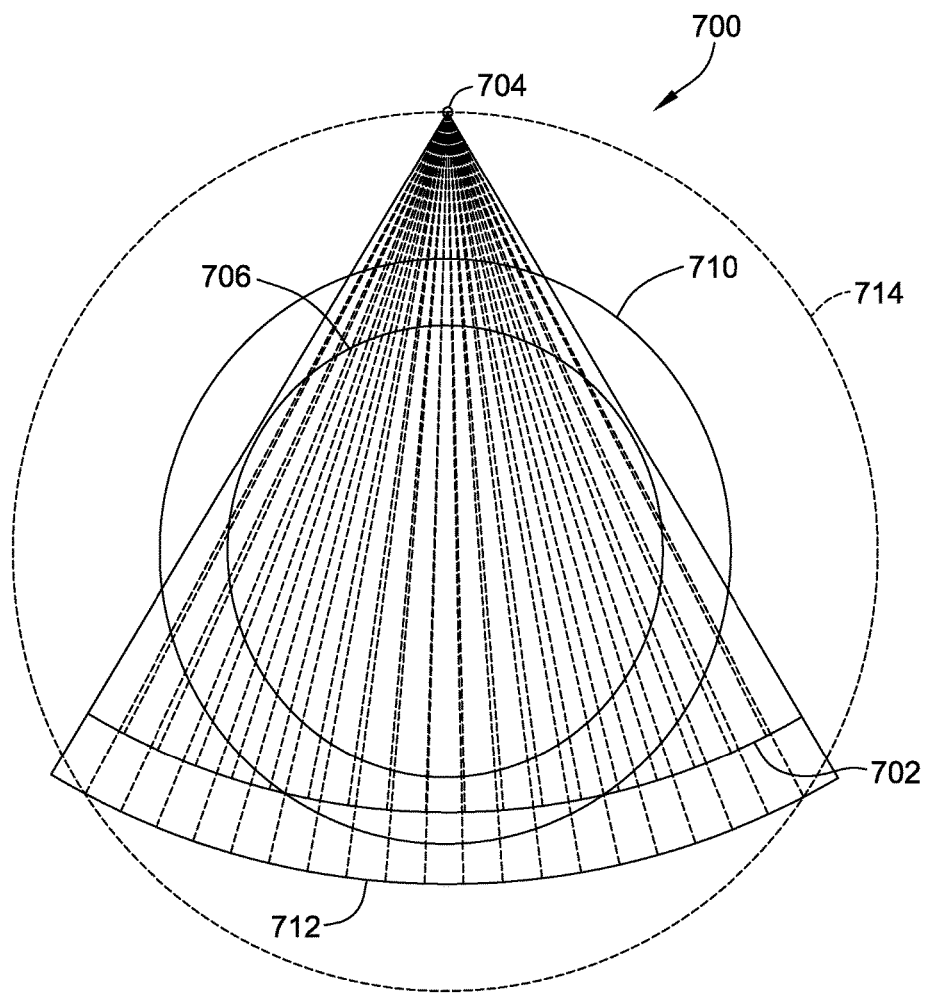

FIG. 9 shows updated detector modules 712 moved further from x-ray source 704 to accommodate second FOV 710. This has a relatively significant impact on the geometry of gantry 700. As shown in FIG. 10, moving the detector modules 702 results in updated detector modules 712 intersecting a path 714 of x-ray source 704. Path 714 controls the physical outer diameter of gantry 700. As the size and weight of gantry 700 will depend roughly quadratically on a radius of path 714, it is important to minimize the radius of path 714. However, as shown in FIG. 10, updated detector modules 712 intersect path 714, and accordingly, gantry 700 will have to become larger because the outer corners of updated detector modules 712 are further from the isocenter than x-ray source 704.

Figure 11:
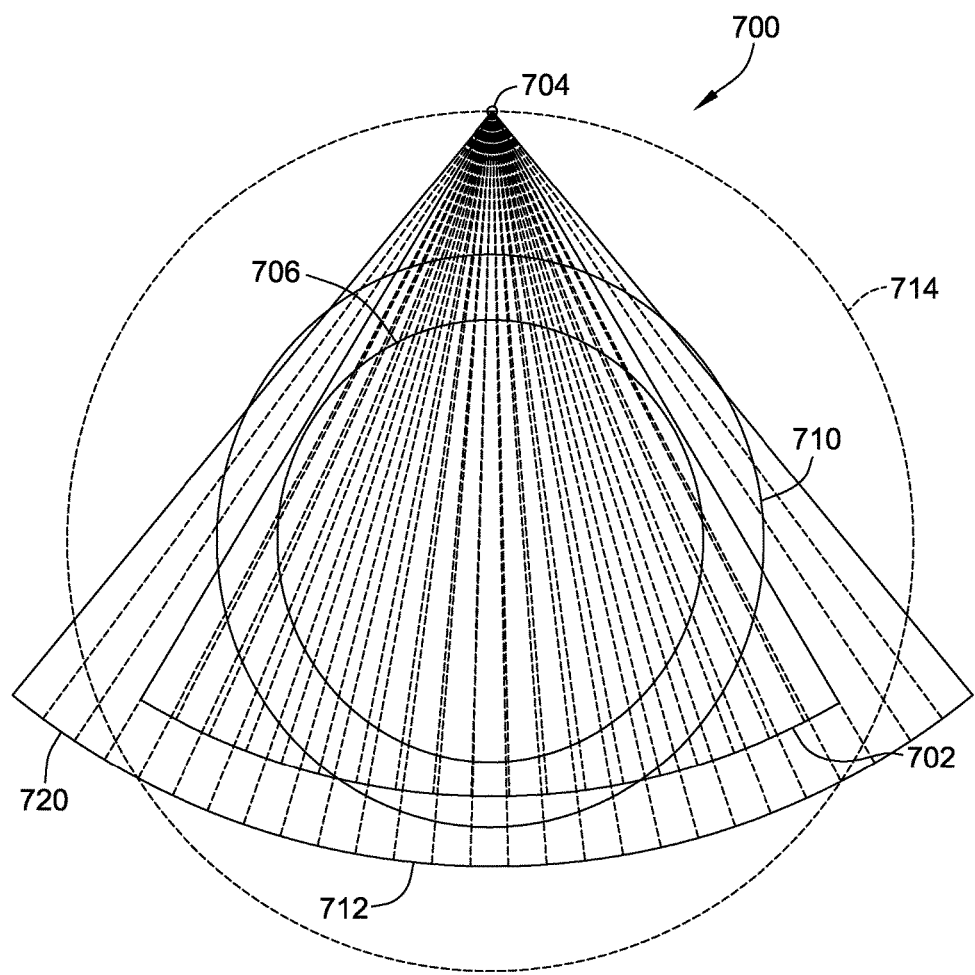

The situation becomes worse when, as shown in FIG. 11, updated detector modules 712 are expanded to form an expanded detector array 720 that is capable of capturing the entire second FOV 710. Here, the detector arc is now significantly larger than path 714. As a result, the outer diameter of gantry 700 must be increased substantially to accommodate second FOV 710. In effect, the only solution is to build a single system with second FOV 710, and use only a subset of expanded detector array 720 to achieve first FOV 706. Because of the use of a traditional (i.e., non-compact) geometry, this results in a gantry that is substantially larger, heavier, and more costly than a gantry designed specifically for first FOV 706.

Figure 12:
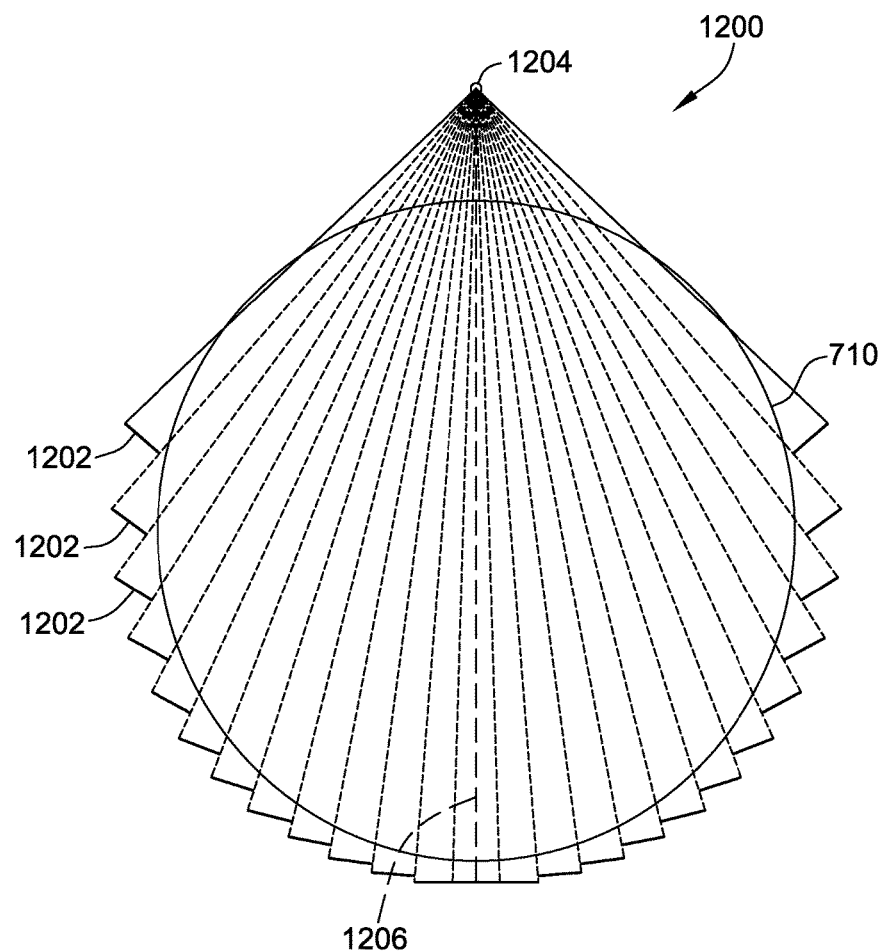

In contrast, FIG. 12 shows a gantry 1200 having detector modules 1202 arranged in a compact geometry. Here, as described above in detail, a distance between an x-ray source 1204 and detector modules 1202 decrease as you move away from a central ray 1206. As shown in FIG. 12, gantry 1200 accommodates second FOV 710. Because x-ray source 1204 is the controlling feature for the outer diameter of gantry 1200, the geometry of gantry 1200 only depends weakly on the desired FOV.

Figure 13:
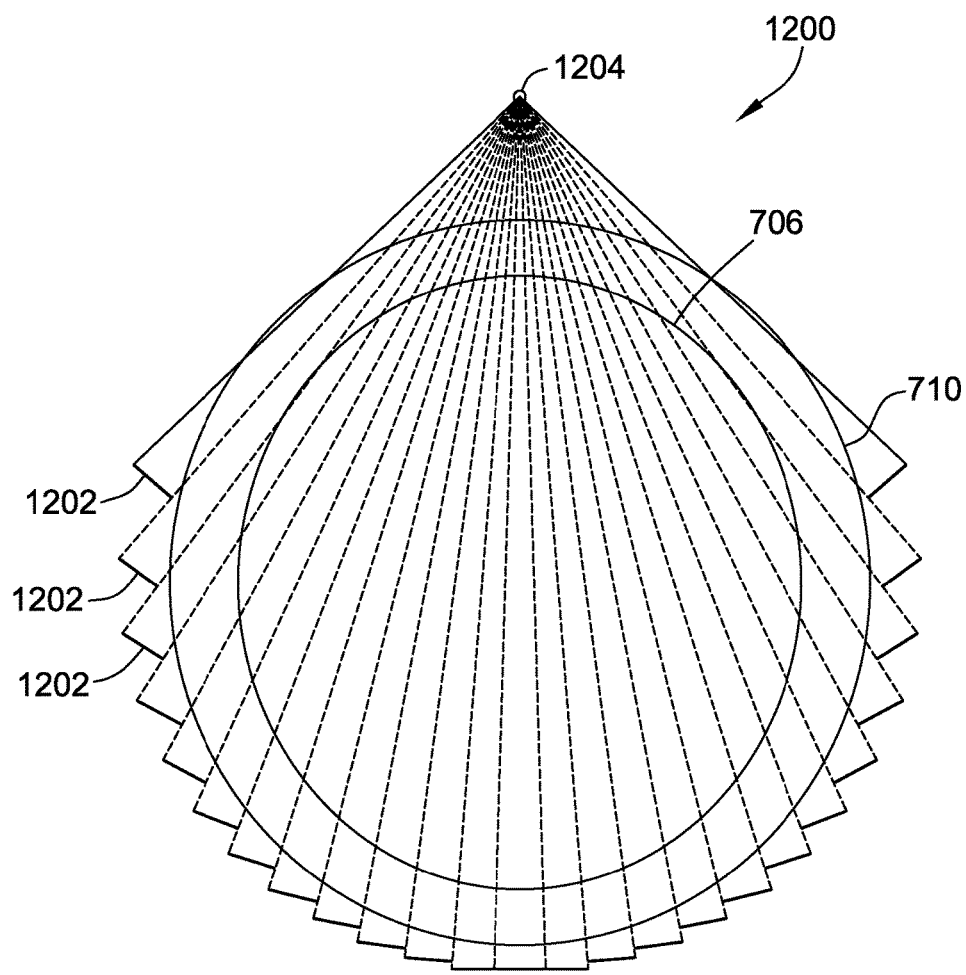
Figure 14:
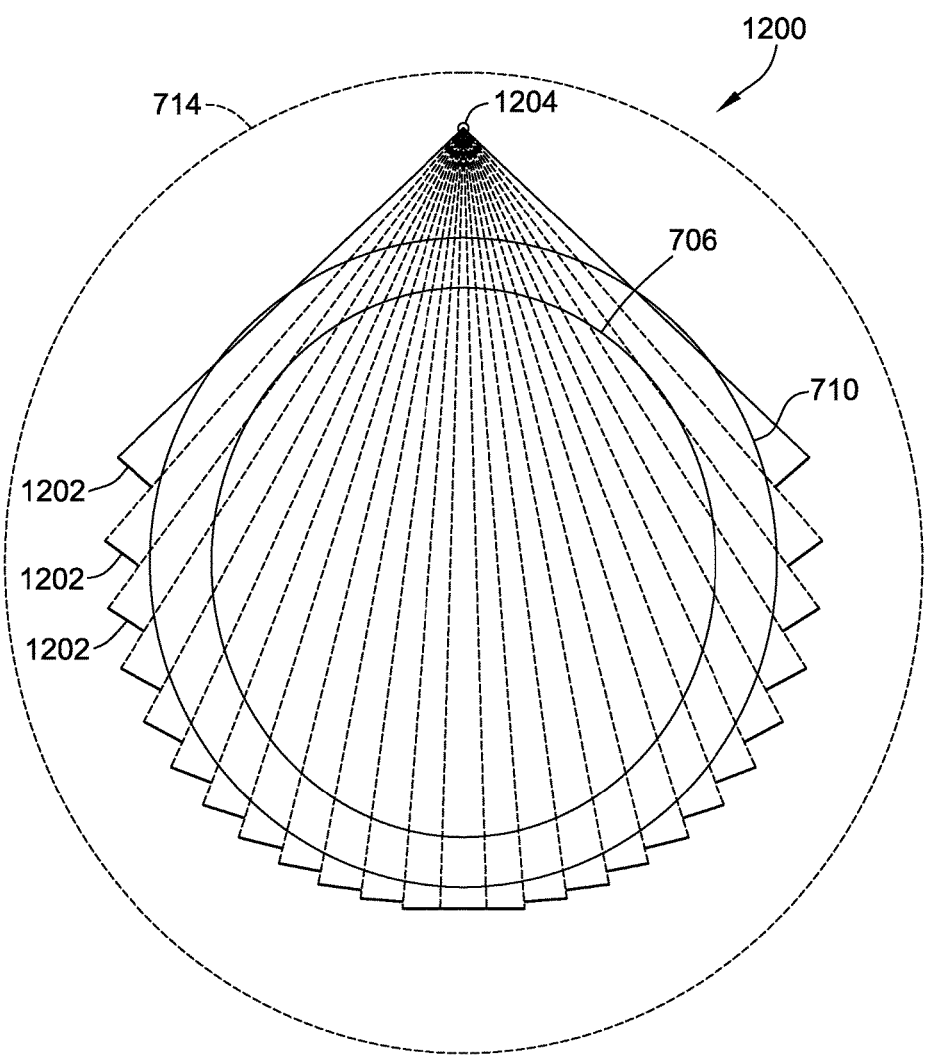

FIG. 13 shows gantry 1200 with both first FOV 706 and second FOV 710. Note that first FOV 706 can be accommodated by excluding the outer two detector modules 1202. Further, FIG. 14 shows path 714 as compared to the geometry of gantry 1200. Notably, as compared to gantry 700, gantry 1200 offers multiple FOVs from a single geometry without significant changes to the outer dimension of gantry 1200.

Figure 15:
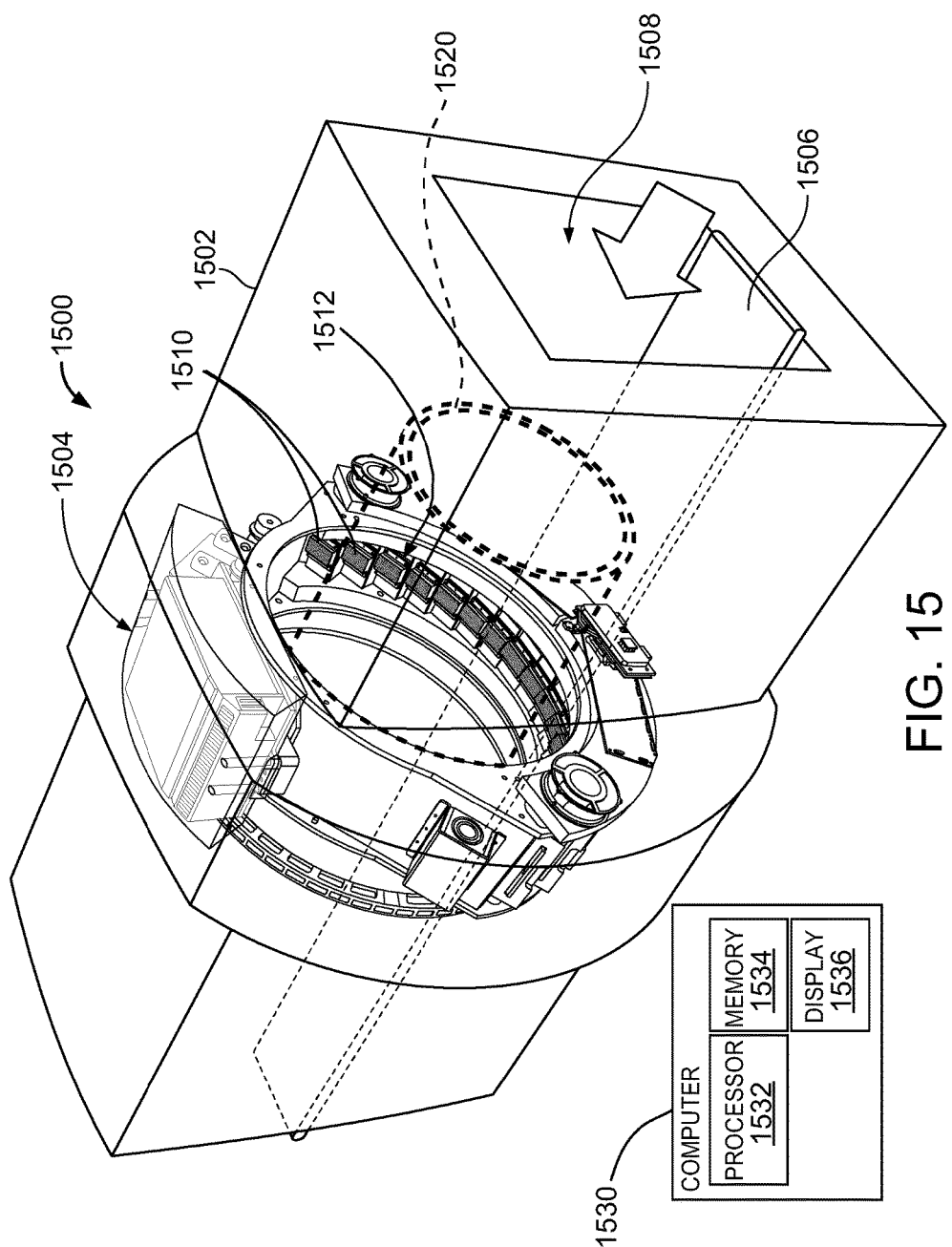
FIG. 15 is a schematic diagram of an exemplary imaging system that is reconfigurable for multiple fields of view.

FIG. 15 is a schematic diagram of an exemplary imaging system 1500 that is reconfigurable for multiple FOVs. As shown in FIG. 15, imaging system 1500 includes an imaging device 1502 having a gantry assembly 1504. Imaging device 1502 includes a conveyor 1506 extending through a tunnel 1508 for imaging objects using gantry assembly 1504.

As shown in FIG. 15, gantry assembly 1504 includes detector modules 1510 of a detector array 1512 arranged in a compact geometry, as described in detail above. To facilitate imaging at multiple FOVs, in the exemplary embodiment, detector modules 1510 are selectively removable and insertable into gantry assembly 1504. Accordingly, for imaging at smaller FOVs, at least a portion of detector modules 1510 (i.e., outer detector modules) may be removed from gantry assembly 1504. Similarly, for imaging at larger FOVs, detector modules 1510 may be added to gantry assembly 1504. Removing detector modules 1510 decreases an arc length of detector array 1512, and adding detector modules 1510 increases an arc length of detector array 1512. In some embodiments, to make detector array 1512 reconfigurable, gantry assembly 1504 may include a detector housing containing locations where detector modules 1510 can be selectively mounted. For a smaller FOV system, selective locations may be left unpopulated, or left with mechanical "blanks" that occupy the holes left by missing detector modules. Alternatively, the detector housing itself could be switched out for one with a different number of locations. If the detector housing is attached to gantry assembly 1504, changing detector housing to accommodate different fields of view can be accomplished relatively easily at the manufacturing location or in the field. The determination of which modules are included is driven by the FOV. For example, detector modules 1510 for which the corresponding x-ray fan beams lie outside the FOV add no value to the image being reconstructed, and can be removed.

Imaging system 1500 further includes an insert 1520 that is positionable within tunnel 1508. Insert 1520 guides objects being scanned so that they are positioned within the appropriate FOV. That is, for different FOVs, the position of conveyor 1506 is the same, but the position of the FOV changes. For example, for smaller FOVs, objects may need to be elevated (e.g., 1-5 inches) above conveyer 1506 to fully lie within the FOV. Accordingly, in some embodiments, imaging system 1500 may include multiple different inserts 1520, with each insert corresponding to a different FOV. In the exemplary embodiment, insert 1520 is a substantially cylindrical sheet metal tube. Alternatively, insert 1520 may be fabricated from any material and/or have any shape that enables imaging system 1500 to function as described herein. For example, in some embodiments, the tube of insert 1520 may have a faceted, rectangular, square, or circular cross-section.

In the exemplary embodiment, imaging system 1500 includes a computer 1530 communicatively coupled to detector modules 1510. Computer 1530 includes a processor 1532, which is communicatively coupled to a memory 1534 and a display 1536. Stored in memory 1534 is data received from detector modules 1510 and instructions for generating images of objects that pass through imaging device 1502. Processor 1532 is capable of executing the instructions stored in memory 1534, and generated images may be displayed on display 1536. Computer 1530 may be physically separate from imaging device 1502 or integrated therein.

It should be understood that processor as used herein means one or more processing units (e.g., in a multi-core configuration). The term processing unit, as used herein, refers to microprocessors, microcontrollers, reduced instruction set circuits (RISC), application specific integrated circuits (ASIC), logic circuits, and any other circuit or device capable of executing instructions to perform functions described herein.

It should be understood that references to memory mean one or more devices operable to enable information such as processor-executable instructions and/or other data to be stored and/or retrieved. Memory may include one or more computer readable media, such as, without limitation, hard disk storage, optical drive/disk storage, removable disk storage, flash memory, non-volatile memory, ROM, EEPROM, random access memory (RAM), and the like.

Additionally, it should be understood that communicatively coupled components may be in communication through being integrated on the same printed circuit board (PCB), in communication through a bus, through shared memory, through a wired or wireless data communication network, and/or other means of data communication. Additionally, it should be understood that data communication networks referred to herein may be implemented using Transport Control Protocol/Internet Protocol (TCP/IP), User Datagram Protocol (UDP), or the like, and the underlying connections may comprise wired connections and corresponding protocols, for example, Institute of Electrical and Electronics Engineers (IEEE) 802.3 and/or wireless connections and associated protocols, for example, an IEEE 802.11 protocol, an IEEE 802.15 protocol, and/or an IEEE 802.16 protocol.

The systems and methods described herein may be used to detect contraband. As used herein, the term "contraband" refers to illegal substances, explosives, narcotics, weapons, special nuclear materials, dirty bombs, nuclear threat materials, a threat object, and/or any other material that a person is not allowed to possess in a restricted area, such as an airport. Contraband may be hidden within a subject (e.g., in a body cavity of a subject) and/or on a subject (e.g., under the clothing of a subject). Contraband may also include objects that can be carried in exempt or licensed quantities intended to be used outside of safe operational practices, such as the construction of dispersive radiation devices.

Exemplary embodiments of methods and systems for imaging an object are described above in detail. The methods and systems are not limited to the specific embodiments described herein, but rather, components of systems and/or steps of the methods may be utilized independently and separately from other components and/or steps described herein. Accordingly, the exemplary embodiment can be implemented and utilized in connection with many other applications not specifically described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A gantry assembly for use with an imaging system, said gantry assembly comprising:
    an x-ray source;
    a modular detector assembly comprising a plurality of selectively removable detector modules, wherein a first detector module of said plurality of detector modules is mounted at a first distance from said x-ray source and a second detector module of said plurality of detector modules is mounted at a second distance from said x-ray source, wherein the first distance is different from the second distance, and wherein said gantry assembly is configured to image objects using both a first field of view and a second field of view that is larger than the first field of view; and
    a tube configured to position an object within the first field of view.

2. A gantry assembly in accordance with claim 1, wherein said tube has at least one of a faceted, rectangular, square, and circular cross-section.

3. A gantry assembly in accordance with claim 1, wherein said x-ray source is configured to travel in a circular path when imaging objects using the first field of view and configured to travel in the same circular path when imaging objects using the second field of view.

4. A gantry assembly in accordance with claim 1, wherein at least one detector module of said plurality of detector modules is configured to be removed from said modular detector array to switch from imaging objects using the second field of view to imaging objects using the first field of view.

5. A gantry assembly in accordance with claim 1, further comprising at least one additional detector module configured to be added to said plurality of detector modules to switch from imaging objects using the first field of view to imaging objects using the second field of view.

6. An imaging system comprising:
    a gantry assembly comprising:
        an x-ray source; and
        a modular detector assembly comprising a plurality of selectively removable detector modules, wherein a first detector module of said plurality of detector modules is mounted at a first distance from said x-ray source and a second detector module of said plurality of detector modules is mounted at a second distance from said x-ray source, wherein the first distance is different from the second distance;
    a conveyor extending through a tunnel defined through said gantry assembly, wherein said imaging system is configured to image objects using both a first field of view and a second field of view that is larger than the first field of view; and
    a tube configured to be positioned between an object and said conveyor, said tube configured to position the object within the first field of view.

7. An imaging system in accordance with claim 6, wherein said tube has at least one of a faceted, rectangular, square, and circular cross-section.

8. An imaging system in accordance with claim 6, wherein said x-ray source is configured to travel in a circular path when imaging objects using the first field of view and configured to travel in the same circular path when imaging objects using the second field of view.

9. An imaging system in accordance with claim 6, wherein at least one detector module of said plurality of detector modules is configured to be removed from said modular detector array to switch from imaging objects using the second field of view to imaging objects using the first field of view.

10. An imaging system in accordance with claim 6, further comprising at least one additional detector module configured to be added to said plurality of detector modules to switch from imaging objects using the first field of view to imaging objects using the second field of view.

11. An imaging system in accordance with claim 6, further comprising a computer communicatively coupled to said plurality of detector modules, said computer configured to generate an image of an object based on data acquired by said plurality of detector modules.

12. A method for imaging an object using a gantry assembly including an x-ray source and a modular detector having a plurality of selectively removable detector modules, wherein a first detector module of the plurality of detector modules is mounted at a first distance from the x-ray source and a second detector module of the plurality of detector modules is mounted at a second distance from the x-ray source, wherein the first distance is different from the second distance, the method comprising:

altering a number of detector modules in the modular detector by one of adding and removing detector modules such that a field of view of the gantry assembly changes from a first size to a second size; and imaging the object using the field of view having the second size.

13. A method in accordance with claim 12, further comprising positioning the object within the gantry assembly using an insert.

14. A method in accordance with claim 13, wherein positioning the object comprises positioning the object using an insert that is a tube.

\* \* \* \* \*